United States Patent [19]

Moroi et al.

[11] Patent Number: 5,258,375
[45] Date of Patent: Nov. 2, 1993

[54] COMPOSITION FOR THE PREPARATION OF DOSAGE-FORM ACTIVE VITAMINS D₃ CONTAINING POLYVINYLACETAL DIETHYLAMINOACETATE

[75] Inventors: Masami Moroi, Yachiyo; Toshio Yokoyama, Tokyo; Akira Iwasa, Yotsukaido; all of Japan

[73] Assignee: SS Pharmaceutical Co., Ltd., Tokyo, Japan

[21] Appl. No.: 3,689

[22] Filed: Jan. 13, 1993

Related U.S. Application Data

[63] Continuation of Ser. No. 491,171, Mar. 9, 1990, abandoned.

[30] Foreign Application Priority Data

Mar. 13, 1989 [JP] Japan ................................. 1-60554

[51] Int. Cl.⁵ .................. A61K 31/595; A61K 47/00; C07J 172/00
[52] U.S. Cl. .................. 514/168; 514/788; 552/653
[58] Field of Search .............. 514/788, 167, 169, 170; 552/653

[56] References Cited

U.S. PATENT DOCUMENTS

| | | | |
|---|---|---|---|
| 1,819,297 | 7/1933 | Kropp et al. | 514/167 |
| 3,089,822 | 5/1963 | Schenk | 514/167 |
| 3,823,237 | 7/1974 | Frank | 514/167 |
| 4,012,509 | 3/1977 | Frank | 514/167 |
| 4,308,264 | 12/1981 | Conway et al. | 514/167 |
| 4,729,895 | 3/1988 | Makino et al. | 424/465 |
| 4,948,788 | 8/1990 | Makino et al. | 514/167 |

FOREIGN PATENT DOCUMENTS

| | | |
|---|---|---|
| 215596 | 3/1987 | European Pat. Off. |
| 1062389 | 7/1959 | Fed. Rep. of Germany |

Primary Examiner—Frederick E. Waddell
Assistant Examiner—T. J. Criares
Attorney, Agent, or Firm—Oblon, Spivak, McClelland, Maier & Neustadt

[57] ABSTRACT

Compositions suitable for use in the preparation of dosage-form active vitamins D₃ are disclosed. Each composition comprises an active vitamin D₃ and a stabilizer selected from polyvinylacetal diethylaminoacetate and hydroxypropylcellulose. Also disclosed are processes for the preparation of stable dosage-form active vitamins D₃. Each process comprises adding the above stabilizer to an active vitamin D₃ and then adding a pharmaceutically-acceptable carrier to the resultant mixture.

4 Claims, No Drawings

COMPOSITION FOR THE PREPARATION OF DOSAGE-FORM ACTIVE VITAMINS $D_3$ CONTAINING POLYVINYLACETAL DIETHYLAMINOACETATE

This application is a continuation of application Ser. No. 07/491,171, filed on Mar. 9, 1990, now abandoned.

BACKGROUND OF THE INVENTION

1) Field of the Invention

The present invention relates to compositions for the preparation of dosage-form active vitamins $D_3$ in which the active vitamins $D_3$ have superb stability.

2) Description of the Related Art

Active vitamins $D_3$ such as $1\alpha$-hydroxyvitamin $D_3$ and $1\alpha,25$-dihydroxyvitamin $D_3$ are known as excellent therapeutic drugs for rickets, osteomalacia and the like. These active vitamins $D_3$ are however very unstable substances, so that they undergo decomposition even at room temperature and cannot be stored for long time even when prepared into dosage forms.

As their stabilization method, it has heretofore been known, for example, to form each active vitamin $D_3$ into a composition by dissolving it in triglyceride (Japanese Patent Application Laid-Open No. 130,905/1977), to add an amino acid as a stabilizer (Japanese Patent Application Laid-Open No. 17/1987) or to form it into a composition by dissolving the same in a propylene glycol fatty acid ester (Japanese Patent Application Laid-Open No. 54323/1988).

These methods are however not fully satisfactory. There has hence been a desire for the development of a still better method for the stabilization of active vitamins $D_3$.

SUMMARY OF THE INVENTION

With the foregoing circumstances in view, the present inventors have carried out an extensive investigation. As a result, it has been found that polyvinylacetal diethylaminoacetate and hydroxypropylcellulose have excellent stabilization effects to active vitamins $D_3$, leading to the completion of the present invention.

In one aspect of the present invention, there is thus provided a composition for the preparation of a dosage-form active vitamin $D_3$, which comprises an active vitamin $D_3$ and a stabilizer selected from polyvinylacetal diethylaminoacetate and hydroxypropylcellulose.

In another aspect of the present invention, there is also provided a method for stabilizing an active vitamin $D_3$, which comprises adding to the active vitamin $D_3$ a stabilizer selected from polyvinylacetal diethylaminoacetate and hydroxypropylcellulose.

In a further aspect of the present invention, there is also provided a process for preparing a stable dosage-form active vitamin $D_3$, which comprises adding to an active vitamin $D_3$ a stabilizer selected from polyvinylacetal diethylaminoacetate and hydroxypropylcellulose and then adding a pharmaceutically-acceptable carrier to the resultant mixture.

According to the present invention, compositions containing an active vitamin $D_3$ with considerably improved stability can be obtained. These compositions are extremely useful for dosage-form preparations.

DETAILED DESCRIPTION OF THE INVENTION AND THE PREFERRED EMBODIMENTS

Exemplary active vitamin $D_3$ useful in the practice of the present invention include those having a hydroxyl group on $1\alpha$-position such as $1\alpha$-hydroxyvitamin $D_3$ ($1\alpha$-OH-$D_3$), $1\alpha,24$-dihydroxyvitamin $D_3$ [$1\alpha,24$-(OH)$_2$-$D_3$], $1\alpha,25$-dihydroxyvitamin $D_3$ [$1\alpha,25$-(OH)$_2$-$D_3$] and $1\alpha,24,25$-trihydroxyvitamin $D_3$ [$1\alpha,24,25$-(OH)$_3$-$D_3$]; and those having no hydroxyl group on $1\alpha$-position such as 24-hydroxyvitamin $D_3$ (24-OH-$D_3$) and 25-hydroxyvitamin $D_3$ (25-OH-$D_3$).

Of the stabilizers usable in the present invention, polyvinylacetal diethylaminoacetate means a polyacetal formed by reacting polyvinyl alcohol and acetaldehyde with the removal of $H_2O$ molecules and then causing diethylaminoacetic acid to form ester bonds with some of the remaining hydroxyl groups. It is represented by the following formula:

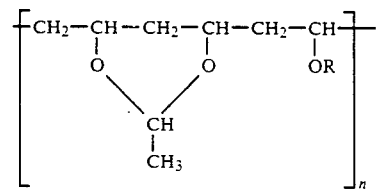

wherein R means H or

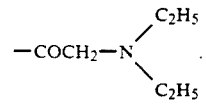

In the present invention, polyvinylacetal diethylaminoacetate and hydroxypropylcellulose can be used either singly or in combination. They may be incorporated in a total proportion of 1–100,000 times by weight the active vitamin $D_3$, with 10–50,000 times by weight being particularly preferred.

The composition of the present invention for the preparation of a dosage-form active vitamin $D_3$ can be produced by blending an active vitamin $D_3$ and polyvinylacetal diethylaminoacetate and/or hydroxypropylcellulose into a uniform mixture. As a preferred production method, the following method may be mentioned. Namely, the composition of the present invention for the preparation of a dosage-form active vitamin $D_3$ can be obtained by dissolving an active vitamin $D_3$ in a solvent capable of dissolving the same, for example, ethanol, propanol, isopropanol or the like, adding polyvinylacetal diethylaminoacetate and/or hydroxypropylcellulose to the solution, thoroughly stirring the resultant mixture into a solution and then distilling off the solvent.

To obtain an active-vitamin-$D_3$-containing drug preparation by using the composition obtained as described above, it is only necessary to combine the composition with a pharmaceutically-acceptable known carrier and/or a pharmaceutically-effective known ingredient and then form them into a dosage form. For example, the combination with pharmaceutically-acceptable carriers known to date makes it possible to provide active vitamin $D_3$ preparations such as tablets, granules and capsules. On the other hand, the combination with pharmaceutically-effective ingredients such as vitamins of other kinds leads to the formation of combined drugs such as vitamin complexes.

Since the stability of the active vitamin $D_3$ in the composition of the present invention has been considerably enhanced owing to the action of the associated stabilizer, the composition can be prepared into dosage forms by conventional dosage preparation methods. Further, the active vitamin $D_3$ can be stored stably after the preparation into the dosage forms.

[Examples]

The present invention will next be described in further detail by the following examples.

Example 1

Two milligrams of $1\alpha$-OH-$D_3$ were dissolved in 50 ml of ethanol so that a solution was prepared. After 2 g of polyvinylacetal diethylaminoacetate ("AEA SANKYO", trade name; product of Sankyo Co., Ltd.) were added to the solution and dissolved therein, ethanol was distilled off under reduced pressure. The residue was dried to obtain 1,900 mg of a composition. The content of $1\alpha$-OH-$D_3$ in the composition was 0.1 wt. %.

Example 2

In a similar manner to Example 1, was produced a composition consisting of a mixture of 2 mg of $1\alpha$-OH-$D_3$ and 2 g of hydroxypropylcellulose ("HPC-L", trade name; product of Nippon Soda Co., Ltd.).

Example 3

In a similar manner to Example 1, was produced a composition consisting of a mixture of 2 mg of $1\alpha$-OH-$D_3$, 1 g of polyvinylacetal diethylaminoacetate ("AEA SANKYO", trade name; product of Sankyo Co., Ltd.) and 1 g of hydroxypropylcellulose ("HPC-L", trade name; product of Nippon Soda Co., Ltd.).

Test 1

The compositions obtained in Examples 1-3 respectively were stored at 50° C. and the percent remainders of $1\alpha$-OH-$D_3$ were investigated 2 weeks and 4 weeks later. Employed as a control was a composition which had been obtained by adding 1 g of lactose to an ethanol solution of 1 mg of $1\alpha$-OH-$D_3$ and then distilling off ethanol under reduced pressure.

Time-dependent changes of the percent remainders of $1\alpha$-OH-$D_3$ in the compositions of the present invention and the control are shown in Table 1. As is clearly envisaged from Table 1, $1\alpha$-OH-$D_3$ in each composition of the present invention is far superior in stability compared with that in the control.

TABLE 1

| Sample | Initial amount, % | Percent remainder after 2 weeks | Percent remainder after 4 weeks |
|---|---|---|---|
| Example 1 | 100.0 | 98.8 | 97.5 |
| Example 2 | 100.0 | 98.4 | 96.2 |
| Example 3 | 100.0 | 98.0 | 95.7 |
| Control | 100.0 | 33.6 | 0.0 |

Example 4

The composition of the present invention, which had been obtained in Example 1, was mixed with other ingredients in accordance with the below-described formula. The resultant mixture was then pressed into vitamin $D_3$ tablets by "KIKUSUI Rotary Tablet Machine" (trade name). The tablets had a diameter of 6 mm, a thickness of about 2 mm and a weight of 85 mg. They contained about 1 μg of $1\alpha$-OH-$D_3$ per tablet.

| (Formula) | |
|---|---|
| Composition of Example 1 | 1.00 g |
| Lactose | 78.05 g |
| Crystalline cellulose | 4.25 g |
| Stearic acid | 1.70 g |

Example 5

The composition of the present invention, which had been obtained in Example 2, was mixed with other ingredients in accordance with the below-described formula. The resultant mixture was then granulated by an extruder ("W-pelleter Model EXR-60", trade name; manufactured by Fuji Paudal Co., Ltd.). The granules were dried at 50° C. and then packaged in stick-like envelopes, whereby a granular vitamin $D_3$ preparation was obtained in the envelopes, each containing 1 g of the granules. The granular preparation contained about 1 μg of $1\alpha$-OH-$D_3$ per envelope.

| (Formula) | |
|---|---|
| Composition of Example 2 | 1.00 g |
| Purified sucrose | 969.00 g |
| Polyvinylpyrrolidone K-90 | 30.00 g |
| Perfume | trace |

Example 6

The composition of the present invention, which had been obtained in Example 3, was mixed with other ingredients in accordance with the below-described formula. The resultant mixture was then granulated by the extruder ("W-pelleter Model EXR-60", trade name; manufactured by Fuji Paudal Co., Ltd.). The granules were rounded into spherical granules in "Marumerizer Model Q-230" (trade name; manufactured by Fuji Paudal Co., Ltd.), dried at 50° C. and then filled in No. 1 capsules at a rate of 350 mg per capsule, whereby capsules were obtained. Those capsules contained about 1 μg of $1\alpha$-OH-$D_3$ per capsule.

| (Formula) | |
|---|---|
| Composition of Example 3 | 1.00 g |
| Purified sucrose | 229.00 g |
| Corn starch | 100.00 g |
| Carboxymethylcellulose | 20.00 g |

We claim:

1. A composition for the preparation of a stable pharmaceutical composition of active vitamin $D_3$, which comprises a uniform mixture of an active vitamin $D_3$ and 1-100,000 times by weight, based on said active vitamin $D_3$, of polyvinylacetal diethylaminoacetate.

2. The composition of claim 1, wherein the proportion of the polyvinylacetal diethylaminoacetate is 10-50,000 times by weight the proportion of the active vitamin $D_3$.

3. A method for stabilizing an active vitamin $D_3$, which comprises adding an effective amount of polyvinylacetal diethylaminoacetate to the vitamin $D_3$ and forming a uniform mixture thereof.

4. A process for preparing a stable pharmaceutical composition containing vitamin $D_3$, which comprises adding an effective amount of polyvinylacetal diethylaminoacetate to an active vitamin $D_3$, forming a uniform mixture thereof, and then adding a pharmaceutically-acceptable carrier to the resultant mixture.

* * * * *